United States Patent
Tracy et al.

(10) Patent No.: US 6,780,434 B2
(45) Date of Patent: *Aug. 24, 2004

(54) CONTROLLED RELEASE OF METAL CATION-STABILIZED INTERFERON

(75) Inventors: Mark A. Tracy, Arlington, MA (US); Howard Bernstein, Cambridge, MA (US); M. Amin Khan, Downingtown, PA (US)

(73) Assignee: Alkermes Controlled Therapeutics, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/092,365

(22) Filed: Mar. 6, 2002

(65) Prior Publication Data

US 2003/0031716 A1 Feb. 13, 2003

Related U.S. Application Data

(63) Continuation of application No. 09/664,299, filed on Sep. 18, 2000, now Pat. No. 6,379,701, which is a continuation of application No. 08/765,558, filed as application No. PCT/US95/07348 on Jun. 7, 1995, now Pat. No. 6,165,508, which is a continuation-in-part of application No. 08/279,784, filed on Jul. 25, 1994, now Pat. No. 5,711,968.

(51) Int. Cl.⁷ .................. A61K 9/10; A61K 47/32; A61K 47/34

(52) U.S. Cl. .................. 424/487; 424/486; 424/488; 424/499

(58) Field of Search .................. 424/486–488, 424/499, 501, 422–23, 426; 530/814–15

(56) References Cited

U.S. PATENT DOCUMENTS

| | | | |
|---|---|---|---|
| 3,928,566 A | 12/1975 | Briggs et al. | 424/94 |
| 4,166,800 A | 9/1979 | Fong | 252/316 |
| 4,252,791 A | 2/1981 | Grossberg | 424/55 |
| 4,530,901 A | 7/1985 | Weissmann | 435/70 |

(List continued on next page.)

FOREIGN PATENT DOCUMENTS

| | | |
|---|---|---|
| EP | 0 123291 A2 | 10/1984 |
| EP | 0 281299 A1 | 9/1988 |
| EP | 0 307097 A2 | 3/1989 |
| EP | 0633020 A1 | 1/1995 |
| WO | WO91/12882 | 9/1991 |
| WO | WO 91/18927 A1 | 12/1991 |
| WO | WO92/11844 | 7/1992 |
| WO | WO93/25221 | 12/1993 |
| WO | WO93/17668 | 3/1994 |
| WO | WO94/12158 | 6/1994 |
| WO | WO94/19373 A1 | 9/1994 |
| WO | WO 96/07339 A1 | 3/1996 |

OTHER PUBLICATIONS

Nagata, S. et al., "Synthesis in *E. Coli* of a Polypeptide with Human Leukocyte Interferon Activity," *Nature*, 284: 316–320 (Mar. 1980).

(List continued on next page.)

*Primary Examiner*—Edward J. Webman
(74) *Attorney, Agent, or Firm*—Hamilton, Brook, Smith & Reynolds, P.C.

(57) ABSTRACT

This invention relates to a composition, and method of forming said composition, for the controlled release of interferon. The controlled release composition of this invention comprises a biocompatible polymer and particles of metal cation-stabilized interferon, wherein the particles are dispersed within the biocompatible polymer. The method of the invention, for producing a composition for the controlled release of interferon, includes dissolving a polymer in a polymer solvent to form a polymer solution, dispersing particles of metal cation stabilized-interferon particles in the polymer solution, and then solidifying the polymer to form a polymeric matrix containing a dispersion of the interferon particles.

10 Claims, 11 Drawing Sheets

U.S. PATENT DOCUMENTS

| | | | |
|---|---|---|---|
| 4,675,189 A | 6/1987 | Kent et al. | 424/490 |
| 4,853,218 A | 8/1989 | Yim et al. | 424/85.7 |
| 4,871,538 A | 10/1989 | Yim et al. | 424/85.7 |
| 4,897,268 A | 1/1990 | Tice et al. | 424/422 |
| 4,962,091 A | 10/1990 | Eppstein et al. | 514/2 |
| 5,019,400 A | 5/1991 | Gombotz et al. | 424/497 |
| 5,126,147 A | 6/1992 | Silvestri et al. | 424/497 |
| 5,192,741 A | 3/1993 | Orsolini et al. | 514/4 |
| 5,413,797 A | 5/1995 | Khan et al. | 424/489 |
| 5,441,734 A | 8/1995 | Reichert et al. | 424/85.7 |
| 5,711,968 A * | 1/1998 | Tracy et al. | |
| 6,087,324 A | 7/2000 | Igari et al. | 514/2 |
| 6,165,508 A * | 12/2000 | Tracy et al. | |
| 6,379,701 B1 * | 4/2002 | Tracy et al. | |

OTHER PUBLICATIONS

Rubinstein, M. "The Structure of Human Interferons," *Biochimica et Biophysica Acta.*, 695: 5–16 (1982).

Cunningham, B.C. et al., "Dimerization of Human Growth Hormone by Zinc," 253: 545–548 (Aug. 2 1991).

Maciel, G. et al., *Chemistry*, D.C. Heath and Company, pp. 156–157, (1978).

* cited by examiner

CONTROLLED RELEASE OF METAL CATION-STABILIZED INTERFERON

RELATED APPLICATIONS

This application is a continuation of U.S. patent application Ser. No. 09/664,299 filed on Sep. 18, 2000 now U.S. Pat. No. 6,379,701 B1, which is a continuation of U.S. patent application Ser. No. 08/765,558, filed Mar. 7, 1997, which is the U.S. National Phase of International Application Number PCT/US95/07348 having an International Filing Date of Jun. 7, 1995 which published in English, now U.S. Pat. No. 6,165,508, which is a Continuation-in-Part of U.S. patent application Ser. No. 08/279,784 filed on Jul. 25, 1994 now U.S. Pat. No. 5,711,968. The entire content of U.S. patent application Ser. No. 08/765,558 is hereby incorporated by reference.

BACKGROUND OF THE INVENTION

Interferon acts to mediate natural immunity to protect against viral infection and to initiate inflammatory reactions that protect against bacterial infections. Interferon has also been shown to be an effective anti-tumor or anticancer agent.

Previously, the administration of interferon has often required frequent subcutaneous injections, given at intervals which resulted in fluctuating medication levels. However, many conditions treated by interferon therapy may respond better to controlled levels of interferon which may provide more effective prophylactic or therapeutic effects.

Attempts to control and sustain medication levels in humans or animals between the administration of doses have more recently included the use of biodegradable polymers as matrices for controlling the release of medicaments. In some cases, biodegradable polymers, under in vivo conditions, exhibited high initial bursts of medicament release and minimal release thereafter.

Furthermore, methods used to form controlled release compositions have often resulted in a loss of activity of the medicament due to the instability of the medicament, chemical interactions between the medicament and the other components contained in, or used in formulating, the controlled release composition, or have resulted in losses of medicament due to the formulation process.

Therefore, a need exists for a means of controlling the release of interferon while not inordinately reducing the activity, or potency, of the interferon released.

SUMMARY OF THE INVENTION

This invention relates to a composition, and method of forming said composition, for the controlled release of interferon. The controlled release composition of this invention comprises a biocompatible polymer and particles of metal cation-stabilized interferon, wherein the particles are dispersed within the biocompatible polymer.

The method of the invention, for producing a composition for the controlled release of interferon, includes dissolving a polymer in a polymer solvent to form a polymer solution, dispersing particles of metal cation-stabilized interferon in the polymer solution, and then solidifying the polymer to form a polymeric matrix containing a dispersion of the metal cation-stabilized interferon particles.

The advantages of a controlled release formulation for interferon include increased patient compliance and acceptance by reducing the number of subcutaneous injections, increased therapeutic benefit by eliminating fluctuations in interferon concentration in blood levels, and potentially lowering the total administered amount of interferon by reducing these fluctuations. The advantages further include a reduction of the loss of the interferon's biological activity which allows for the use of a lower amount of interferon to form a controlled release composition.

DETAILED DESCRIPTION OF THE INVENTION

Figure 1:
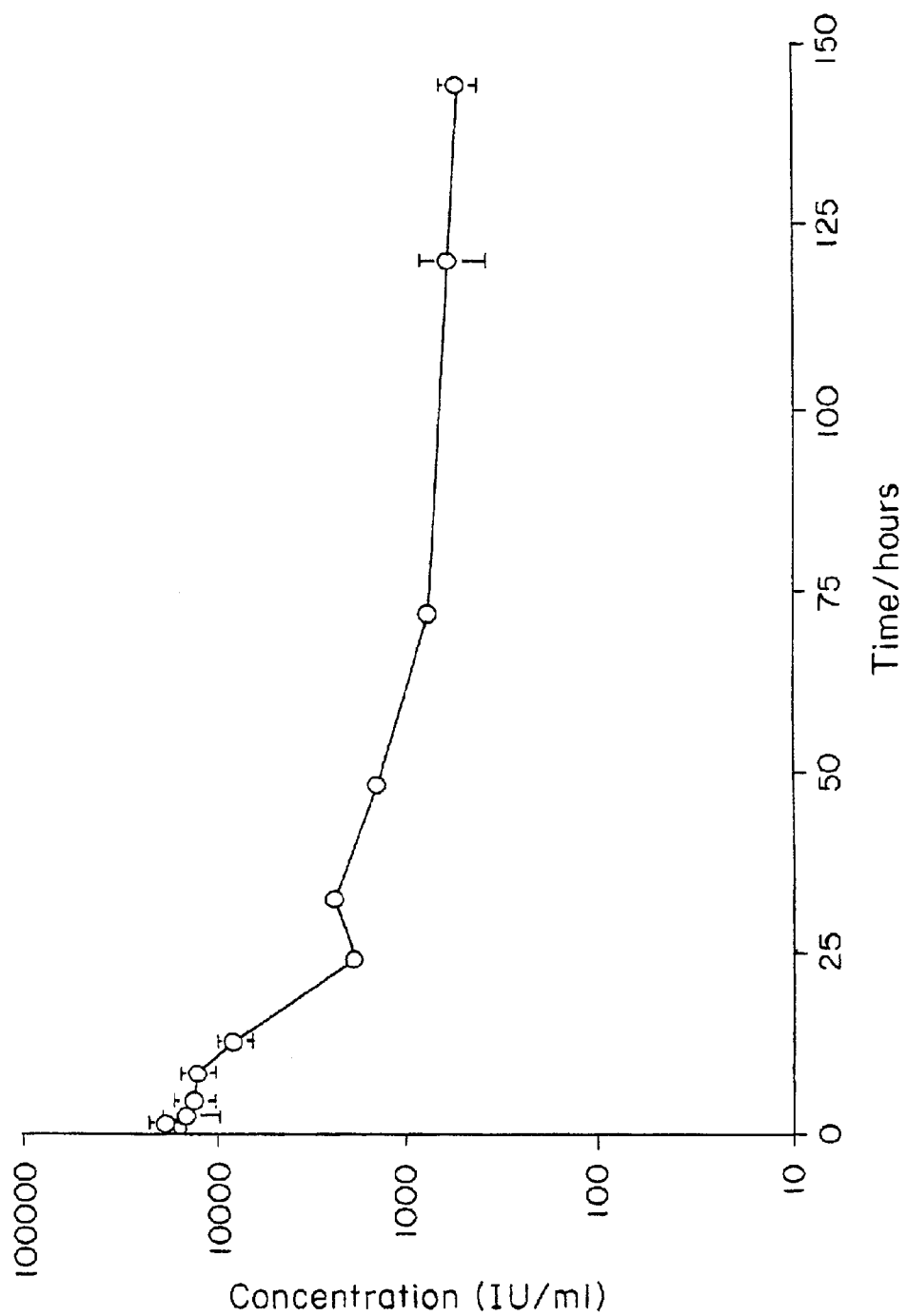
FIG. 1 is a plot of the serum concentration (IU/ml) of Interferon-$\alpha$,2b (IFN-$\alpha$,2b) in rats, which were subcutaneously administered IFN-$\alpha$,2b controlled release microspheres of Example 2, versus time over a 6 day interval.
Figure 2:
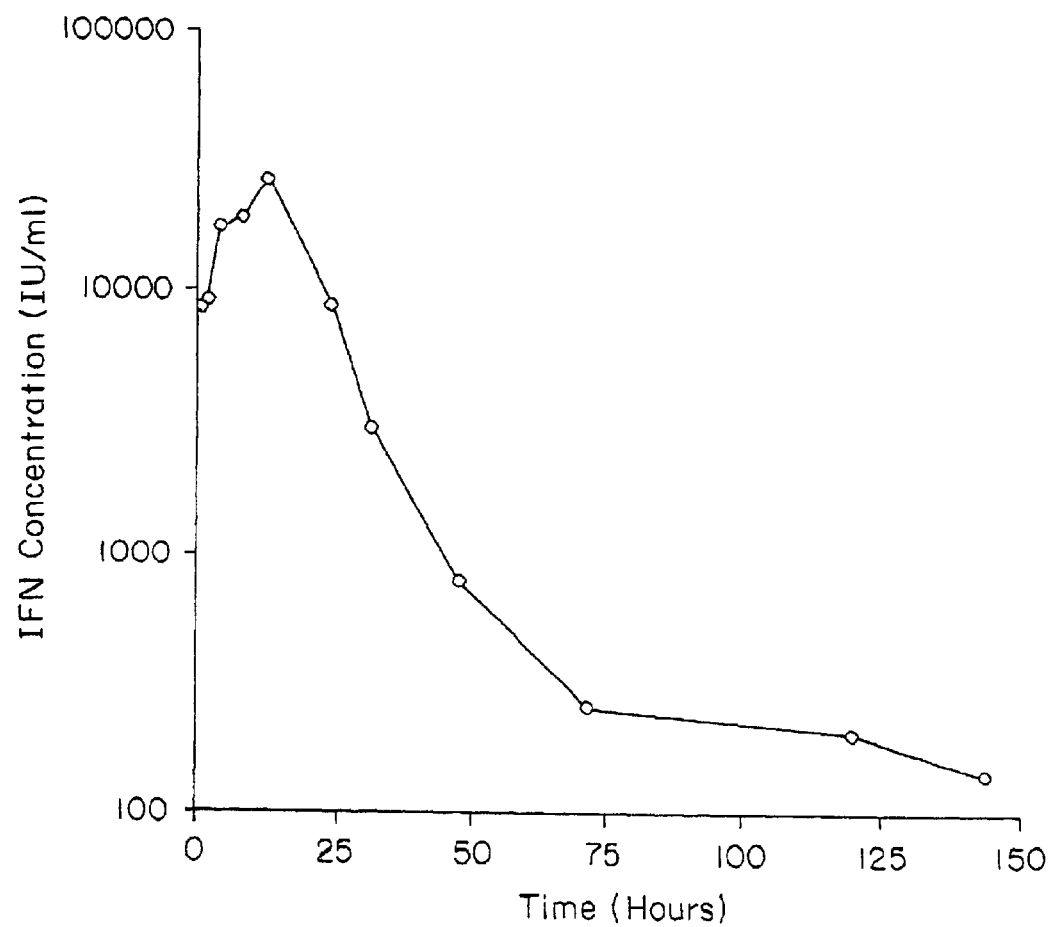
FIG. 2 is a plot of the serum concentration (IU/ml) of IFN-$\alpha$,2b in rats, which were subcutaneously administered IFN-$\alpha$,2b controlled release microspheres of Example 3, versus time over a 6 day interval.
Figure 3:
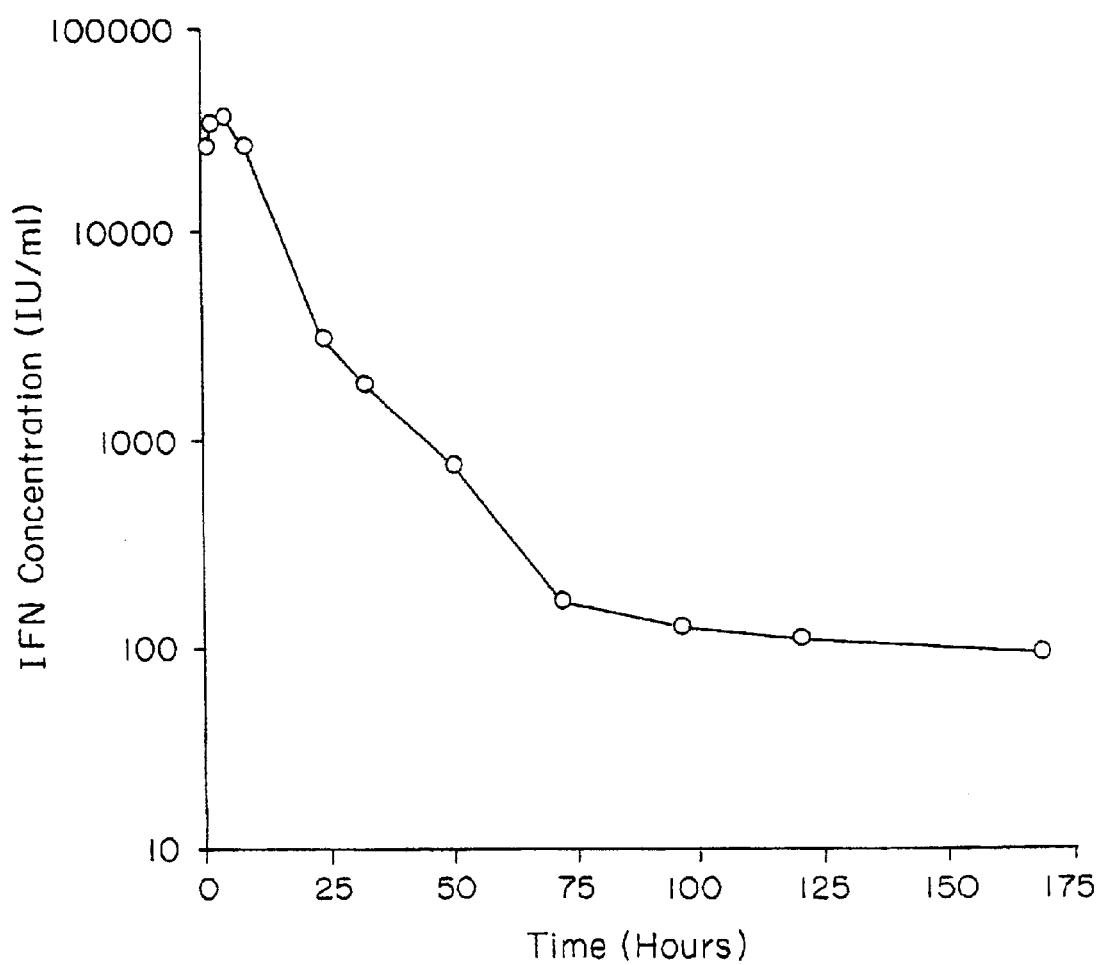
FIG. 3 is a plot of the serum concentration (IU/ml) of IFN-$\alpha$,2b in rats, which were subcutaneously administered IFN-$\alpha$,2b controlled release microspheres of Example 4, versus time over a 7 day interval.
Figure 4:
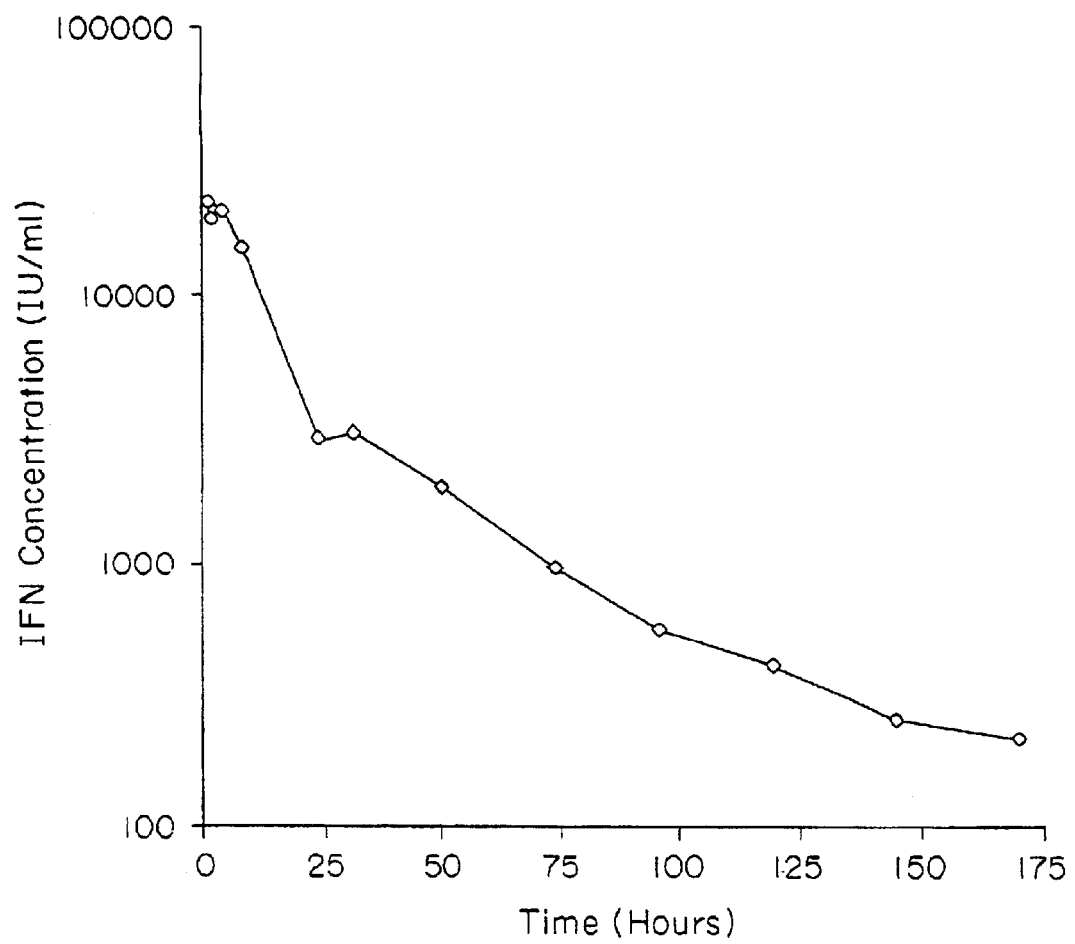
FIG. 4 is a plot of the serum concentration (IU/ml) of IFN-$\alpha$,2b in rats, which were subcutaneously administered IFN-$\alpha$,2b controlled release microspheres of Example 5, versus time over a 7 day interval.
Figure 5:
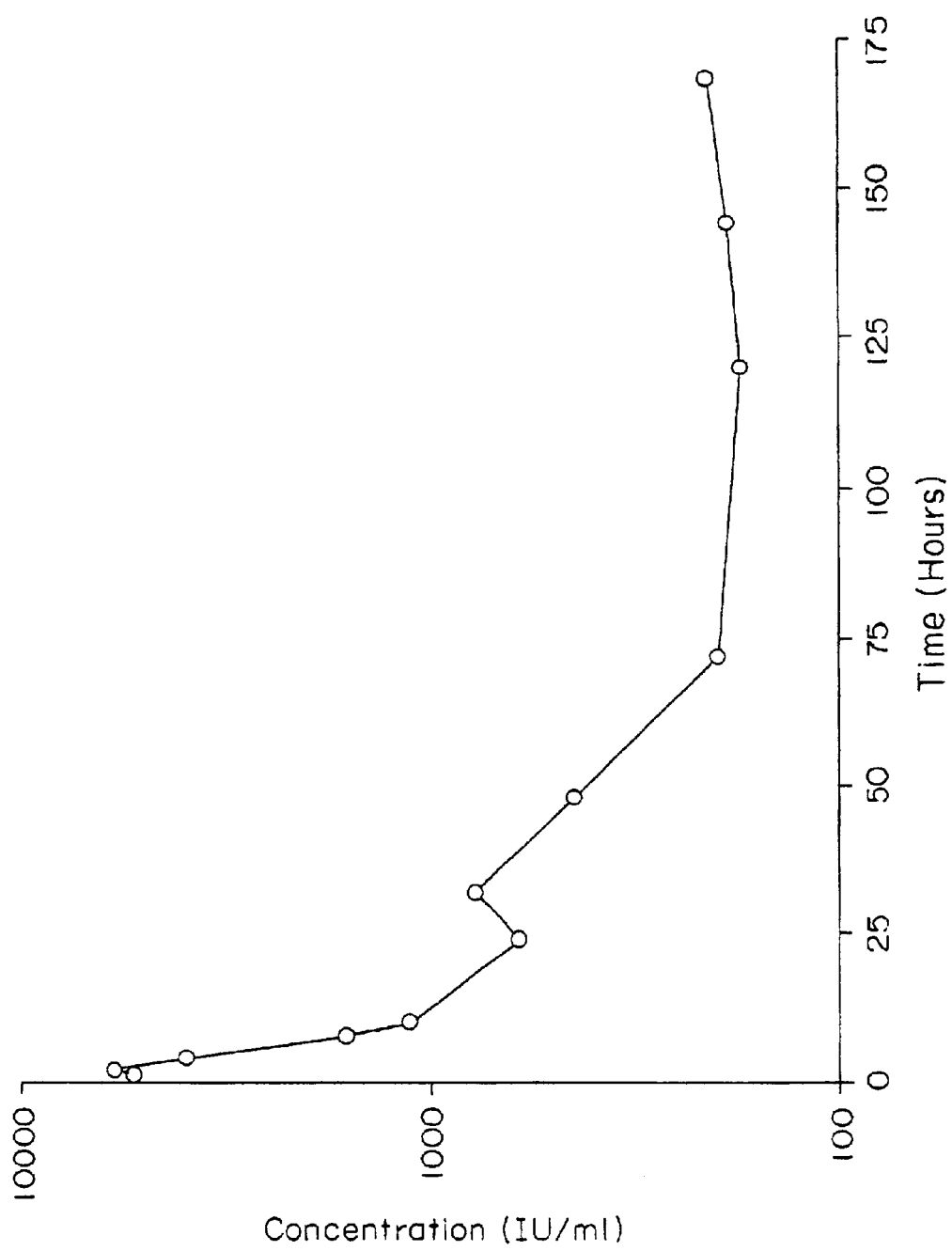
FIG. 5 is a plot of the serum concentration (IU/ml) of IFN-$\alpha$,2b, in rats, which were subcutaneously administered IFN-$\alpha$,2b controlled release microspheres of Example 6, versus time over a 7 day interval.
Figure 6:
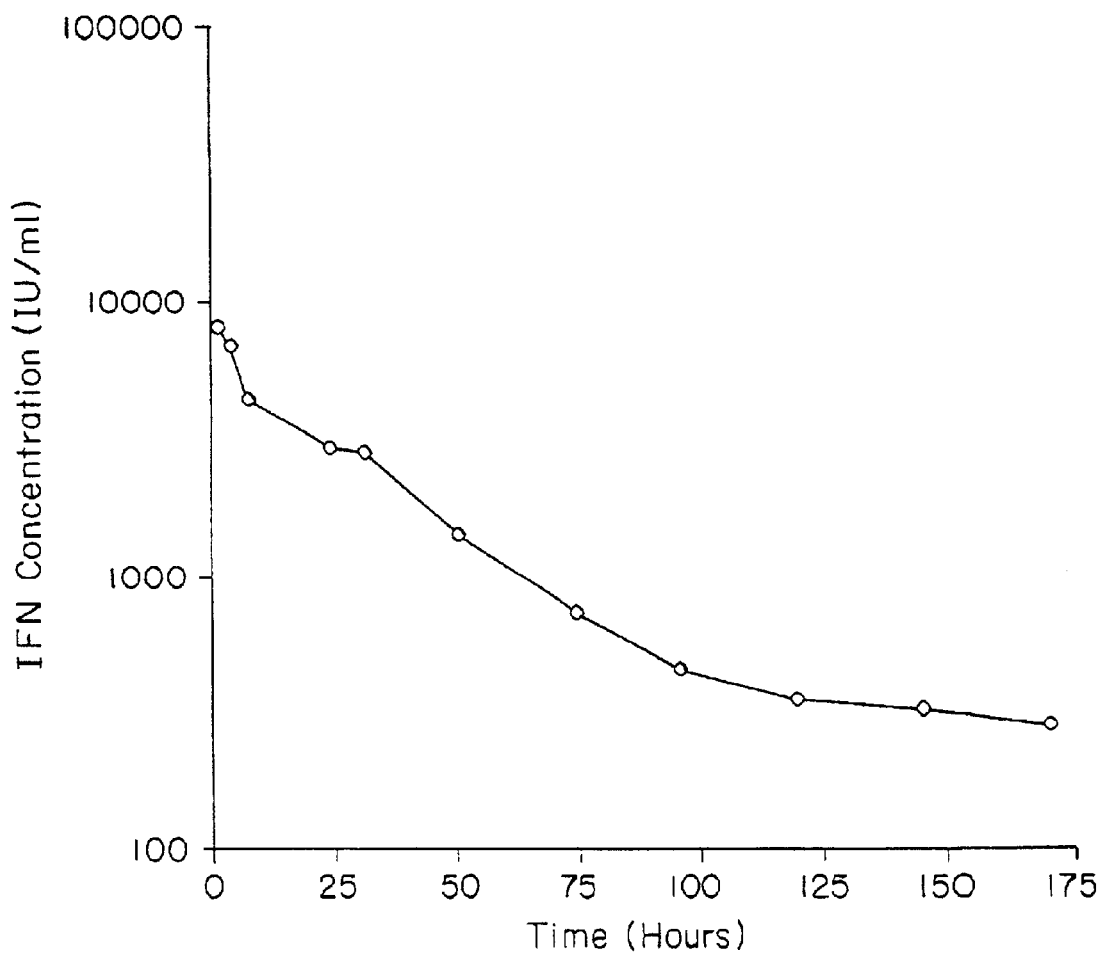
FIG. 6 is a plot of the serum concentration (IU/ml) of IFN-$\alpha$,2b in rats, which were subcutaneously administered IFN-$\alpha$,2b controlled release microspheres of Example 7, versus time over a 7 day interval.
Figure 7:
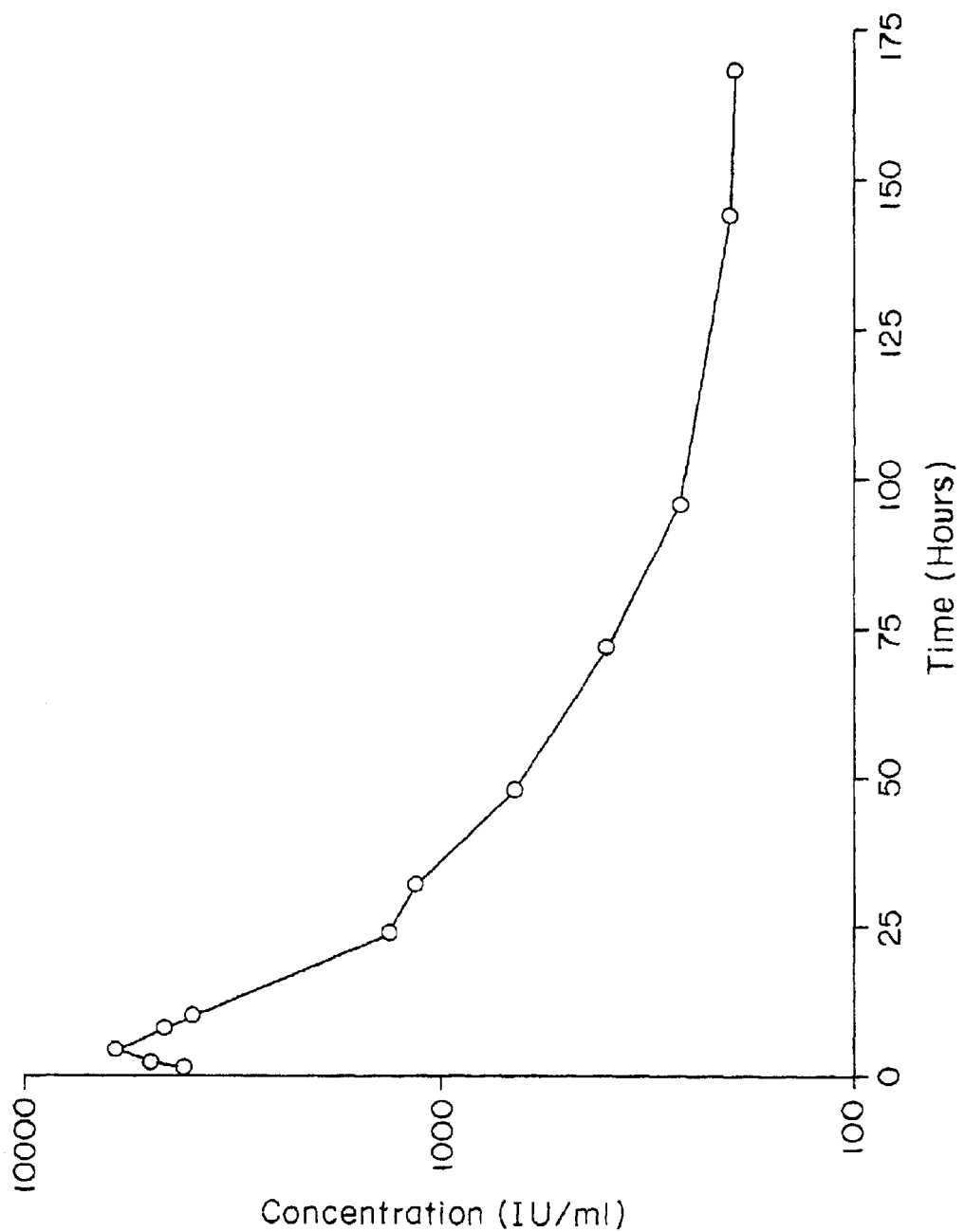
FIG. 7 is a plot of the serum concentration (IU/ml) of IFN-$\alpha$,2b versus time over a 7 day interval in rats which were subcutaneously administered IFN-$\alpha$,2b controlled release microspheres of Example 8 having a 1: zinc carbonate-to-IFN-$\alpha$,2b ratio.

A description of preferred embodiments of the invention follows.

Interferon (IFN), as defined herein, includes all forms of IFN, such as IFN-α, IFN-β and IFN-γ. IFN can be derived from animal sources or can be cloned and purified as described in Rubenstein et al., *Biochem. Biophys. Acta*, 695: 705–716 (1982), Nagata et al., *Nature*, 284: 316–320 (1980), U.S. Pat. No. 4,289,690, issued to Pestka et al and U.S. Pat. No. 4,530,901, issued to C. Weissmann.

As defined herein, a controlled release of interferon is a sustained and/or modulated release of IFN from a biocompatible polymeric matrix. In a sustained release, IFN release occurs over a period which is longer than that period during which a biologically significant amount of IFN would be released following direct administration of a solution of IFN. It is preferred that a sustained release be a release of IFN over a period of up to about one week to about six months. A sustained release of IFN from a polymeric matrix can be continuous or non-continuous release with relatively constant or varying rates of release. The continuity of IFN release and level of IFN release can be affected by use of one or more types of polymer compositions, IFN loadings, and/or selection of excipients to produce the desired effect.

In a modulated IFN release, which results, for example, when a suitable metal cation component is dispersed within the polymeric matrix, at least one IFN release characteristic, such as the initial IFN release level, the subsequent IFN release levels, duration of release and/or the amount of IFN released, is different from the release characteristics exhibited by IFN being released from a polymeric matrix, wherein the polymeric matrix does not contain a dispersed metal cation component.

Metal cation-stabilized interferon (hereinafter "$M^{+n}$-stabilized IFN"), as defined herein, comprises a particle containing biologically active IFN and at least one type of multivalent metal cation, having a valency of +2 or more, wherein the cation is not significantly oxidizing to IFN. Thus for $M^{+n}$, n is an integer equal to 2 or more. It is preferred that the $M^{+n}$ be complexed with the IFN. In $M^{+n}$-stabilized IFN, the tendency of IFN to aggregate within a microparticle during hydration and/or to lose biological activity or potency due to the process of forming a controlled release composition or due to the chemical characteristics of a controlled release composition, is reduced by mixing metal cations ($M^{+n}$) with the IFN prior to forming $M^{+n}$-stabilized IFN particles. The $M^{+n}$-stabilized IFN particles are subsequently dispersed within a polymeric matrix to form a controlled release composition of this invention.

Suitable IFN-stabilizing metal cations include biocompatible multivalent metal cations which will not significantly oxidize IFN. Typically, oxidation of IFN by a metal cation is not significant if this oxidation results in a loss of IFN potency of about 10% or less. A metal cation is biocompatible if the cation is non-toxic to the recipient, in the quantities used, and also presents no significant deleterious or untoward effects on the recipient's body, such as an immunological reaction at the injection site.

Examples of suitable IFN-stabilizing metal cations include cations of non-transition metals, such as $Mg^{+2}$ and $Ca^{+2}$. Suitable IFN-stabilizing metal cations also include cations of transition metals, such as $Cu^{+2}$. In a preferred embodiment, $Zn^{+2}$ is used as a IFN-stabilizing metal cation. The suitability of metal cations for stabilizing IFN can be determined by one of ordinary skill in the art by performing a variety of stability indicating techniques such as polyacrylamide gel electrophoresis, isoelectric focusing, reverse phase chromatography, HPLC and potency tests on IFN lyophilized particles containing metal cations to determine the potency of the IFN after lyophilization and for the duration of release from microparticles, as described in Examples 9–13.

Polymers suitable to form a polymeric matrix of the controlled release composition of this invention are biocompatible polymers which can be either a biodegradable or non-biodegradable polymers, or blends or copolymers thereof.

Biodegradable, as defined herein, means the composition will degrade or erode in vivo to form smaller chemical species. Degradation can result, for example, by enzymatic, chemical and physical processes. Suitable biocompatible, biodegradable polymers include, for example, poly(lactides), poly(glycolides), poly(lactide-coglycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetals, polycyanoacrylates, polyetheresters, poly(dioxanone)s, poly(alkylene alkylate)s, copolymers of polyethylene glycol and polyorthoester, biodegradable polyurethanes, blends and copolymers thereof.

Biocompatible, non-biodegradable polymers suitable for the modulated release composition of this invention include non-biodegradable polymers selected from the group consisting of polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

A polymer, or polymeric matrix, is biocompatible if the polymer, and any degradation products of the polymer, are non-toxic to the recipient and also present no significant deleterious or untoward effects on the recipient's body, such as an immunological reaction at the injection site.

Further, the polymer can be blocked, unblocked or a blend of blocked and unblocked polymers. A blocked polymer is as classically defined in the art, specifically having blocked carboxyl end groups. Generally, the blocking group is derived from the initiator of the polymerization and is typically an alkyl group. An unblocked polymer is as classically defined in the art, specifically having free carboxyl end groups.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weights is of about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 5,000 Daltons to about 42,000 Daltons The amount of IFN, which is contained in the $M^{+n}$-stabilized IFN particles dispersed within the polymeric matrix of a controlled release composition is a therapeutically or prophylactically effective amount, which can be determined by a person of ordinary skill in the art taking into consideration factors such as body weight, condition to be treated, type of polymer used, and release rate from the polymer.

In one embodiment, an IFN controlled release composition will contain from about 0.01% (w/w) to approximately 50% (w/w) IFN of the dry weight of the composition. The amount of IFN used will vary depending upon the desired effect of the IFN, the planned release levels, and the time span over which the IFN will be released. A preferred range of IFN loading is between about 0.1% (w/w) to about 30% (w/w) IFN. A more preferred range of IFN loading is between about 0.5% (w/w) to about 15% (w/w) IFN.

In another embodiment, an IFN controlled release composition also contains a second metal cation component, which is not contained in the $M^{+n}$-stabilized IFN particles, but which is dispersed within the polymer. The second metal cation component can optionally contain the same species of metal cation, as is contained in the $M^{+n}$-stabilized IFN, and/or can contain one or more different species of metal cation. The second metal cation component acts to modulate the release of the IFN from the polymeric matrix of the controlled release composition and can enhance the stability of IFN in the composition. A metal cation component used in modulating release typically comprises at least one type of multivalent metal cations. Examples of second metal cation components suitable to modulate IFN release, include, or contain, for instance, $Mg(OH)_2$, $MgCO_3$ (such as $4MgCO_3.Mg(OH)_2.5H_2O$), $ZnCO_3$ (such as $3Zn(OH)_2.2ZnCO_3$), $CaCO_3$, $Zn_3(C_6H_5O_7)_2$, $Mg(OAc)_2$, $MgSO_4$, $Zn(OAc)_2$, $ZnSO_4$, $ZnCl_2$, $MgCl_2$ and $Mg_3(C_6H_5O_7)_2$. A suitable ratio of second metal cation component-to-polymer is between about 1:99 to about 1:2 by weight. The optimum ratio depends upon the polymer and the second metal cation component utilized. A polymeric matrix containing a dispersed metal cation component to modulate the release of a biologically active agent from the polymeric matrix is further described in U.S. Pat. No. 5,656,297 to Bernstein, et al. and published PCT Patent Application WO 95/29664, the teachings of which are incorporated herein by reference in their entirety.

In yet another embodiment, at least one pore forming agent, such as a water soluble salt, sugar or amino acid, is included in the microparticle to modify the microstructure of the microparticle. The proportion of pore forming agent added to the polymer solution is between about 1% (w/w) to about 30% (w/w). It is preferred that at least one pore forming agent be included in a nonbiodegradable polymeric matrix of the present invention.

The interferon in an IFN controlled release composition can also be mixed with other excipients, such as stabilizers, solubility agents and bulking agents. Stabilizers are added to maintain the potency of the IFN over the duration of IFN release. Suitable stabilizers include, for example, carbohydrates, amino acids, fatty acids and surfactants and are known to those skilled in the art. The amount of stabilizer used is based on the ratio to the IFN on a weight basis. For amino acids, fatty acids and carbohydrates, such as sucrose, lactose, mannitol, dextran and heparin, the molar ratio of carbohydrate to IFN is typically between about 1:10 and about 20:1. For surfactants, such as Tween™ and Pluronic™, the molar ratio of surfactant to IFN is typically between about 1:1000 and about 1:20.

Solubility agents are added to modify the solubility of IFN. Suitable solubility agents include complexing agents, such as albumin and protamine, which can be used to affect the release rate of IFN from a polymeric matrix. The weight ratio of solubility agent to IFN is generally between about 1:99 and about 20:1.

Bulking agents typically comprise inert materials. Suitable bulking agents are known to those skilled in the art.

The IFN controlled release composition of this invention can be formed into many shapes, such as a film, a pellet, a cylinder, a disc or a microparticle. A microparticle, as defined herein, comprises a polymeric component having a diameter of less than about one millimeter and having $M^{+n}$-stabilized IFN particles dispersed therein. A microparticle can have a spherical, non-spherical or irregular shape. It is preferred that a microparticle be a microsphere. Typically, the microparticle will be of a size suitable for injection. A preferred size range for microparticles is from about 1 to about 180 microns in diameter.

In the method of this invention for forming an IFN controlled release composition, a suitable amount of $M^{+n}$-stabilized IFN particles is dispersed within a polymer solution. The IFN particles can be dispersed with the polymer solution by stirring, agitation, sonication or by other known mixing means. The polymer solution, having a dispersion of $M^{+n}$-stabilized IFN particles is then solidified, by appropriate means, to form an IFN controlled release composition of this invention.

Alternately, particles of $M^{+n}$-stabilized IFN and a polymer can be mixed into a polymer solvent sequentially, in reverse order, intermittently, separately or through concurrent additions, to form a dispersion of $M^{+n}$-stabilized IFN particles in a polymer solution.

A suitable polymer solution contains between about 1% (w/w) and about 30% (w/w) of a suitable biocompatible polymer, wherein the biocompatible polymer is typically dissolved in a suitable polymer solvent. Preferably, a polymer solution contains about 5% (w/w) to about 20% (w/w) polymer. A polymer solution containing 10% to about 15% (w/w) polymer is most preferred.

A suitable polymer solvent, as defined herein, is solvent in which the polymer is soluble but in which the $M^{+n}$-IFN particles are substantially insoluble and non-reactive. Examples of suitable polymer solvents include polar organic liquids, such as methylene chloride, chloroform, ethyl acetate and acetone.

To prepare $M^{+n}$-stabilized IFN particles, interferon is mixed in a suitable solvent with at least one suitable IFN-stabilizing metal cation to form a $M^{+n}$-IFN mixture, wherein each component of the mixture can be in suspension or solution, or a combination thereof. In forming $M^{+n}$-stabilized IFN, the molar ratio of $M^{+n}$:IFN in solution is typically between about 1:2 and about 100:1, and is preferentially between about 1:1 and about 10:1. The concentration of IFN in solution is typically between about 0.1 to about 20 mg IFN/ml of solvent, and preferentially, between about 1.0 to about 5.0 mg IFN/ml of solvent.

It is understood that the IFN can be in a solid or a dissolved state, prior to being contacted with the metal cation component. It is also understood that the metal cation component can be in a solid or a dissolved state, prior to being contacted with the IFN. In a preferred embodiment, a buffered aqueous solution of IFN is mixed with an aqueous solution of the metal cation component.

Suitable solvents are those in which the IFN and the metal cation component are each at least slightly soluble, such as in an aqueous sodium bicarbonate buffer or in an aqueous phosphate buffer. For aqueous solvents, it is preferred that water used be either deionized water or water-for-injection (WFI).

The $M^{+n}$-IFN mixture is then dried, such as by lyophilization, to form particulate $M^{+n}$-stabilized IFN. The $M^{+n}$-IFN mixture can be bulk lyophilized or can be divided into smaller volumes which are then lyophilized. In a preferred embodiment, the $M^{+n}$-IFN mixture is micronized, such as by use of an ultrasonic nozzle, and then lyophilized to form $M^{+n}$-stabilized IFN particles. Acceptable means to lyophilize the $M^{+n}$-IFN mixture include those known in the art.

In a preferred embodiment, interferon is contacted with at least one suitable IFN-stabilizing metal cation, such as $Ca^{+2}$, and with a suitable solvent, under pH conditions suitable for forming a complex of $M^{+n}$ and IFN. Typically, the $M^{+n}$-complexed IFN will be in the form of a cloudy precipitate, which is suspended in the solvent. However, the $M^{+n}$-complexed IFN can also be in solution. In an even more preferred embodiment, IFN is complexed with $Zn^{+2}$.

Suitable pH conditions to form a complex of $M^{+n}$ and IFN typically include pH values between about 4.0 and about 8.0. A preferred pH range is between about 5.0 and about 7.4. Suitable pH conditions are typically achieved through use of an aqueous buffer, such as sodium bicarbonate, as the solvent for the IFN and metal cation component. The synthesis of $Zn^{+2}$-stabilized IFN particles is further described in Example 1. Additional description of microspheres containing $Zn^{+2}$-stabilized IFN particles is provided in Examples 2–4.

In one embodiment of the method of this invention, a suitable amount of $M^{+n}$-stabilized IFN particles is added to a polymer solution. In another embodiment, a second metal cation component, which is not contained in $M^{+n}$-stabilized IFN particles, is also dispersed within the polymer solution.

It is understood that a second metal cation component and $M^{+n}$-stabilized IFN can be dispersed into a polymer solution sequentially, in reverse order, intermittently, separately or through concurrent additions. Alternately, a polymer, a second metal cation component and $M^{+n}$-stabilized IFN can be mixed into a polymer solvent sequentially, in reverse order, intermittently, separately or through concurrent additions. The method for forming a composition for modulating the release of a biologically active agent from a biodegradable polymer is further described in co-pending U.S. patent application Ser. No. 08/237,057. Further description of microspheres containing $Zn^{+2}$-stabilized IFN particles and a second metal cation component is provided in Examples 5–8.

One suitable method for forming an IFN controlled release composition from a polymer solution is the solvent evaporation method described in U.S. Pat. No. 3,737,337, issued to Schnoring et al., U.S. Pat. No. 3,523,906, issued to Vranchen et al., U.S. Pat. No. 3,691,090, issued to Kitajima et al., or U.S. Pat. No. 4,389,330, issued to Tice et al. Solvent evaporation is typically used as a method to form IFN controlled release microparticles.

In the solvent evaporation method, a polymer solution containing an $M^{+n}$-stabilized IFN particle dispersion, is mixed in or agitated with a continuous phase, in which the polymer solvent is partially miscible, to form an emulsion. The continuous phase is usually an aqueous solvent. Emulsifiers are often included in the continuous phase to stabilize the emulsion. The polymer solvent is then evaporated over a period of several hours or more, thereby solidifying the polymer to form a polymeric matrix having a dispersion of $M^{+n}$-stabilized IFN particles contained therein.

A preferred method for forming IFN controlled release microparticles from a polymer solution is described in U.S. Pat. No. 5,019,400, issued to Gombotz et al. and U.S. Pat. No. 5,922,253 to Herbert, et al., the teachings of which are incorporated herein in their entirety by reference. This method of microsphere formation, as compared to other methods, such as phase separation, additionally reduces the amount of interferon required to produce a controlled release composition with a specific interferon content and also minimizes the loss of IFN activity during microparticle formation. Also see Examples 2–8 for additional descriptions of microparticle formulations by this method.

In this method, the polymer solution, containing the $M^{+n}$-stabilized IFN particle dispersion, is processed to create droplets, wherein at least a significant portion of the droplets contain polymer solution and $M^{+n}$-stabilized IFN particles. These droplets are then frozen by means suitable to form microparticles. Examples of means for processing the polymer solution dispersion to form droplets include directing the dispersion through an ultrasonic nozzle, pressure nozzle, Rayleigh jet, or by other known means for creating droplets from a solution.

Means suitable for freezing droplets to form microparticles include directing the droplets into or near a liquified gas, such as liquid argon and liquid nitrogen to form frozen microdroplets which are then separated from the liquid gas. The frozen microdroplets are then exposed to a liquid non-solvent, such as ethanol, or ethanol mixed with hexane or pentane. The solvent in the frozen microdroplets is extracted as a solid and/or liquid into the non-solvent to form $M^{+n}$-stabilized IFN containing microparticles. Mixing ethanol with other non-solvents, such as hexane or pentane, can increase the rate of solvent extraction, above that achieved by ethanol alone, from certain polymers, such as poly (lactide-co-glycolide) polymers.

A wide range of sizes of IFN controlled release microparticles can be made by varying the droplet size, for example, by changing the ultrasonic nozzle diameter. If very large microparticles are desired, the microparticles can be extruded through a syringe directly into the cold liquid. Increasing the viscosity of the polymer solution can also increase microparticle size. The size of the microparticles produced by this process can vary over a wide range, for example, from greater than about 1000 to about 1 micrometers, or less, in diameter.

Yet another method of forming an IFN controlled release composition, from a polymer solution, includes film casting, such as in a mold, to form a film or a shape. For instance, after putting the polymer solution containing a dispersion of $M^{+n}$-stabilized IFN particles into a mold, the polymer solvent is then removed by means known in the art, or the temperature of the polymer solution is reduced, until a film or shape, with a consistent dry weight, is obtained. Film casting of a polymer solution, containing a biologically active agent, is further described in U.S. Pat. No. 5,656,297.

The method of this invention for forming an IFN controlled release composition can also be used to form a controlled release composition of another cytokine, wherein the cytokine is similarly susceptible to agglomeration during hydration and/or to a loss of activity, or potency, due to the process of formation or the chemical characteristics of the controlled release composition.

It is believed that the release of the IFN can occur by two different mechanisms. The IFN can be released by diffusion through aqueous filled channels generated in the polymeric matrix, such as by the dissolution of the IFN or by voids created by the removal of the polymer's solvent during the synthesis of the controlled release composition. A second mechanism is the release of IFN due to degradation of the polymer.

The rate of polymer degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; the polymer end group; and the molecular weight of the polymer. These properties can affect hydrophilicity and crystallinity, which control the rate of hydration of the polymer. Hydrophilic excipients such as salts, carbohydrates and surfactants can also be incorporated to increase hydration and which can alter the rate of erosion of the polymer.

By altering the properties of the polymer, the contributions of diffusion and/or polymer degradation to IFN release can be controlled. For example, increasing the glycolide content of a poly(lactide-co-glycolide) polymer and decreasing the molecular weight of the polymer can enhance the hydrolysis of the polymer and thus, provides an increased IFN release from polymer erosion.

In addition, the rate of polymer hydrolysis is increased in non-neutral pH's. Therefore, an acidic or a basic excipient can be added to the polymer solution, used to form the microsphere, to alter the polymer erosion rate.

The composition of this invention can be administered to a human, or other animal, by injection, implantation (e.g, subcutaneously, intramuscularly, intraperitoneally, intracranially, intravaginally and intradermally), administration to mucosal membranes (e.g., intranasally or by means of a suppository), or in situ delivery (e.g. by enema or aerosol spray) to provide the desired dosage of IFN based on the known parameters for treatment with IFN of the various medical conditions.

The invention will now be further and specifically described by the following examples.

EXAMPLE 1

Formation of $Zn^{+2}$-Stabilized Interferon

IFN-α,2b, which was used in the present Examples, is identical to IFN-α,2 as described in Rubenstein et al., *Biochem. Biophys. Acta,* 695: 705–716 (1982), with the exception that the lysine at position 23 of IFN-α,2 is an arginine in IFN-α,2b. The IFNα,2b was dissolved in different volumes of 10 mM sodium bicarbonate buffer (pH 7.2) to form IFN solutions with concentrations between 0.1 and 0.5 mM IFN. A 10 mM $Zn^{+2}$ solution was prepared from deionized water and zinc acetate dihydrate and then was added to the IFN solutions to form $Zn^{+2}$-IFN solutions with a final IFN concentration of about 1.3 mg/ml and a $Zn^{+2}$:IFN molar ratio of 2:1, 4:1 or 10:1, respectively. The pH of the $Zn^{+2}$-IFN solution was then adjusted to 7.1 by adding 1% acetic acid. A cloudy suspended precipitate, comprising $Zn^{+2}$-stabilized IFN, formed in each solution.

The suspension of $Zn^{+2}$-stabilized IFN was then micronized using an ultrasonic nozzle (Type VIA; Sonics and Materials, Danbury, Conn.) and sprayed into a polypropylene tub (17 cm diameter and 8 cm deep) containing liquid nitrogen to form frozen particles. The polypropylene tub was then placed into a −80° C. freezer until the liquid nitrogen evaporated. The frozen particles, which contained $Zn^{+2}$-stabilized IFN, were then lyophilized to form $Zn^{+2}$-stabilized IFN particles.

EXAMPLE 2

Preparation of Blocked PLGA Microspheres Containing a 2:1 $Zn^{+2}$:IFN Molar Ratio Blocked PLGA (0.42 g) with an intrinsic viscosity of 0.15 dl/g, obtained from Birmingham Polymers, Birmingham, Ala., was dissolved in 4.2 ml of methylene chloride to form a polymer solution. To this polymer solution was added 80 mg of lyophilized $Zn^{+2}$-stabilized IFN particles, containing 2 moles of zinc ions per mole of IFN and about 19 mg of sodium bicarbonate.

The polymer solution and $Zn^{+2}$-stabilized IFN particles were then sonicated using an ultrasonic probe (Virtis, Co., Gardiner, N.Y.) to fragment and suspend $Zn^{+2}$stabilized IFN particles in the polymer solution. The size of the sonicated, $Zn^{+2}$stabilized IFN particles was between 2–6 microns. The IFN suspension was then placed in a 10 ml gas-tight syringe.

A 168 ml volume of 100% ethanol was added to the round polypropylene tub. This solution was frozen by surrounding the tub with liquid nitrogen. The frozen ethanol was then covered with 500 ml of liquid nitrogen. The IFN suspension was then pumped from the syringe by a syringe pump (Orion Sage Pump Model 355, Orion Research Inc., Boston, Mass.), at a rate of 1.7 ml/min, into an ultrasonic nozzle (Type VIA, Sonics and Materials, Danbury, Conn.) that was placed above the container containing the frozen ethanol covered with liquid nitrogen. The nozzle atomized the IFN suspension into droplets which froze upon contact with the liquid nitrogen and formed microspheres which sank to the surface of the frozen ethanol.

The container was placed into a −80° C. freezer, thereby evaporating the liquid nitrogen and allowing the ethanol to melt. As the ethanol thawed, the microspheres sank into it. The temperature was lowered to −95.1° C. and the methylene chloride was extracted from the microspheres. After 24 hours, an additional 168 ml of 100% ethanol, which was prechilled to −80° C., was added to the container. Three days after the microspheres were prepared, the ethanol/microsphere slurry was filtered using a 0.65 micron Durapore™ membrane (Millipore, Bedford, Mass.). The filtered microspheres were then vacuum dried in a lyophilizer.

EXAMPLE 3

Preparation of Blocked PLGA Microspheres Containing a 4:1 $Zn^{+2}$:IFN Molar Ratio Blocked PLGA microspheres were prepared according to the method described in Example 2, with the exception that the 80 mg of $Zn^{+2}$-stabilized IFN particles, which were synthesized as described in Example 1 and then added to the polymer solution, contained 4 moles of $Zn^{+2}$ per mole of IFN and 18 mg of sodium bicarbonate.

EXAMPLE 4

Preparation of Blocked PLGA Microspheres Containing a 10:1 Zn:IFN Molar Ratio

Blocked PLGA microspheres were prepared according to the method described in Example 2, with the exception that 0.504 g of blocked PLGA was dissolved in 5.04 ml of methylene chloride to form a polymer solution. To this polymer solution was added 96 mg of $Zn^{+2}$-stabilized IFN particles containing 10 moles of zinc ions per mole of IFN, which were synthesized as described in Example 1, and 18 mg of sodium bicarbonate.

Additionally, the IFN suspension was sprayed into a container containing 202 ml of 100% ethanol, covered with liquid nitrogen. After 24 hours, an additional 202 ml of 100% ethanol, which was prechilled to −80° C., was added to the container.

EXAMPLE 5

Preparation of Blocked PLGA Microspheres Containing Magnesium Carbonate and a 2:1 $Zn^{+2}$:IFN Molar Ratio Blocked PLGA microspheres were prepared according to the method described in Example 2, with the exception that 40 mg of $Zn^{+2}$-stabilized IFN particles, containing 2 moles of zinc ions per mole of IFN, synthesized as described in Example 1, and 9.5 mg of sodium bicarbonate, were added to the polymer solution. In addition, 40 mg of magnesium carbonate, obtained from Spectrum Chemical Manufacturing Corp., (Gardena, Calif.), and sieved through a 38 micron (#400) sieve, was also added to the polymer solution. After sonicating the polymer solution, the size of the sonicated, $Zn^{+2}$-stabilized IFN particles, and of other particles, was between 3–15 microns.

EXAMPLE 6

Preparation of Unblocked PLGA Microspheres Containing Magnesium Carbonate and a 2:1 $Zn^{+2}$:IFN Molar Ratio Unblocked PLGA microspheres were prepared according to the methods described in Example 5 with the exception that 14 mg of $Zn^{2+}$-stabilized IFN particles, containing 2 moles of zinc ions per mole of IFN, synthesized as described in Example 1, and 3.3 mg of sodium bicarbonate were added to the unblocked polymer solution. A hydrophilic unblocked PLGA (0.436g), having an intrinsic viscosity of 0.17 dl/g, was obtained from Boehringer Ingelheim Chemicals, Inc., Montvale, N.J.

In addition, 50 mg of sieved magnesium carbonate was also added to the polymer solution (4.36 ml). Further, two 174 ml aliquots of ethanol were used in the extracting methylene chloride from the microspheres.

EXAMPLE 7

Preparation of Blocked PLGA Microspheres Containing Zinc Carbonate and a 2:1 $Zn^{+2}$:IFN Molar Ratio Blocked PLGA microspheres were prepared according to the method described in Example 2, with the exception that 0.436 g of PLGA was dissolved in 4.36 ml of methylene chloride to form a polymer solution. To this solution was added 14 mg of $Zn^{+2}$-stabilized IFN particles containing 2 moles of zinc ions per mole of IFN and 3.3 mg of sodium bicarbonate. Also, 50 mg of zinc carbonate was sieved through a 38 micrometers sieve and was then added to the polymer solution.

In addition, the IFN suspension was sprayed into a container containing 174 ml of frozen 100% ethanol. Furthermore, after 24 hours an additional 174 ml of 100% ethanol, which was prechilled to −80° C., was added to the container.

This method of preparation resulted in microspheres containing a $ZnCO_3$:IFN mass ration of 3:1.

EXAMPLE 8

Preparation of Blocked PLGA Microspheres Containing Varying Amounts of Zinc Carbonate and a 2:1 $Zn^{+2}$:IFN Molar Ratio Microspheres with a $ZnCO_3$:IFN mass ratio of 1:1 and 8:1 were prepared according to the methods described in Examples 2 and 7, with the exception that 0.410 g of blocked PLGA was dissolved in 4.10 ml of methylene chloride to form a polymer solution. Microspheres with a 1:1 mass ratio were prepared by adding 40 mg of $Zn^{+2}$-stabilized IFN particles, containing 2 moles of zinc ions per mole of IFN and 10.0 mg of sodium bicarbonate. Additionally, 50 mg of zinc carbonate was added to the polymer solution.

The microspheres containing an 8:1 zinc cation:IFN ratio were prepared by adding 7 mg of 2:1 $Zn^{+2}$-stabilized±FN particles and 85 mg of zinc carbonate to the polymer solution.

Each IFN suspension was then sprayed into separate containers, each containing 164 ml of frozen ethanol covered with liquid nitrogen as in previous examples. After 24 hours, additional 164 ml aliquots of 100% ethanol, which were prechilled to −80° C., were added to the separate containers.

The preferred IFN microsphere formulation has a mass weight ratio of zinc carbonate to IFN of 1:1.

EXAMPLE 9

Comparison of IFN Encapsulated with Non-Metal Cation Stabilizers to $Zn^{+2}$-Stabilized IFN Dextran 70 (Spectrum Chemical Manufacturing Co., Gardena, Calif.) was added to a solution of IFN-α,2b in 10 mM sodium phosphate buffer at a weight ratio of 1:1 (Dextran:IFN). The solution was micronized through an ultrasonic nozzle as described in Example 1 and the frozen particles were then lyophilized. The IFN dextran particles were subsequently microencapsulated in blocked PLGA as described in Example 2 to form IFN-Dextran microspheres. $Zn^{+2}$-stabilized IFN particles (2:1 $Zn^{+2}$:IFN ratio) were also microencapsulated as described in Example 2 to form $Zn^{+2}$-stabilized IFN micro spheres.

In vitro dissolution was conducted on the two microsphere formulations by incubating 20 mg of each type of microsphere in buffer at 37° C. IFN release from the microspheres was monitored by BioRad protein assay (BioRad Inc. Richmond, Calif.).

IFN release from the IFN/Dextran microspheres was linear for the first 10 days with an average release rate of 6.4%/day. The release continued at a rate of 0.4%/day from day 10 to day 14 with a total cumulative release of 66% by day 14. No further release of protein from the microspheres was detected. The microspheres were dried down at day 28. The IFN/Dextran remaining was extracted from the microspheres and the protein was characterized by testing its solubility in water and monomer content by sodium dodecyl sulfate (SDS) polyacrylamide gel electrophoresis (PAGE). Only 18% of the protein remaining inside the microspheres was water soluble. The insoluble protein was solubilized using SDS and run on a gel. The insoluble material contained 19% covalent aggregates and 81% non-covalent aggregates.

In contrast the microspheres with the $Zn^{+2}$-stabilized IFN showed linear release for at least 28 days at a rate of 2.7%/day. The analyses indicate the formulation of IFN with zinc is more stable resulting in a longer period of continuous release of protein from the microspheres.

EXAMPLE 10

In vivo Release of IFN-α,2b from Polymeric Microspheres in Rats

Microspheres, containing $Zn^{+2}$-stabilized IFN, which were prepared as described in Examples 2–8, were tested in rats for the in vivo release of IFN-α,2b. Normal rats were obtained from Taconics, Inc. (Germantown, N.Y.). The animals were fed with a standard diet and allowed free access to water. Three to four rats were injected subcutaneously in the interscapular region with a dose of 0.6–2.0 mg of IFN/kg on day 0 for each of the IFN microspheres of Examples 2–8. Blood samples were taken from the tail vein of each rat at 1, 2, 4, 8, 10 (optionally), 24, 36 and 48 hours after injection. Additional blood samples were then taken approximately once a day for the following 4–5 days. The IFN-α concentration in the rat serum samples was determined using an IFN-α immunoradiometric assay, (Celltech, Slough, U.K), hereinafter "IRMA". The IRMA assay has a minimum limit of detecting of 6 IU/ml. The IFN-α,2b serum levels for control rats, which did not receive the microspheres containing $Zn^{+2}$-stabilized IFN were found to be less than 6 IU/ml.

The results of the IRMA assays conducted on the rats receiving the microspheres of Examples 2–7, and the preferred formulation of Example 8, are shown in FIGS. 1–7, respectively. FIGS. 1–7 show that these injectable microsphere formulations provided a sustained release of immunologically active IFN-α.

EXAMPLE 11

Effect of Zinc Carbonate on Release Levels of IFN-α,2b in Rats

Rats (N=4) in three test groups were injected, as described in Example 10, with the microspheres of Example 7 and of Example 8. The dose of IFN for each rat was about 0.8 mg/kg.

The purpose of the test was to determine if the initial burst and sustained level of IFN-α,2b released in vivo can be varied by changing the weight ratio of zinc carbonate to IFN-α,2b in microspheres as described in Example 8.

The weight ratio of zinc carbonate to IFN in microspheres tested for initial burst effects were 0:1, 1:1, 3:1 and 8:1. The tests found that the addition of zinc carbonate to the formulation reduces initial burst in vivo. Specifically, initial bursts measured, as a percentage of the total IFN in the microspheres which were released over the first 24 hours, for microspheres having weight ratios of 0:1, 1:1, 3:1 and 8:1 were 35±13%, 23±7%, 13±5% and 8±1%, respectively.

These initial burst results suggest that the amount of metal cation in the polymer can be used to vary the burst.

Figure 8:
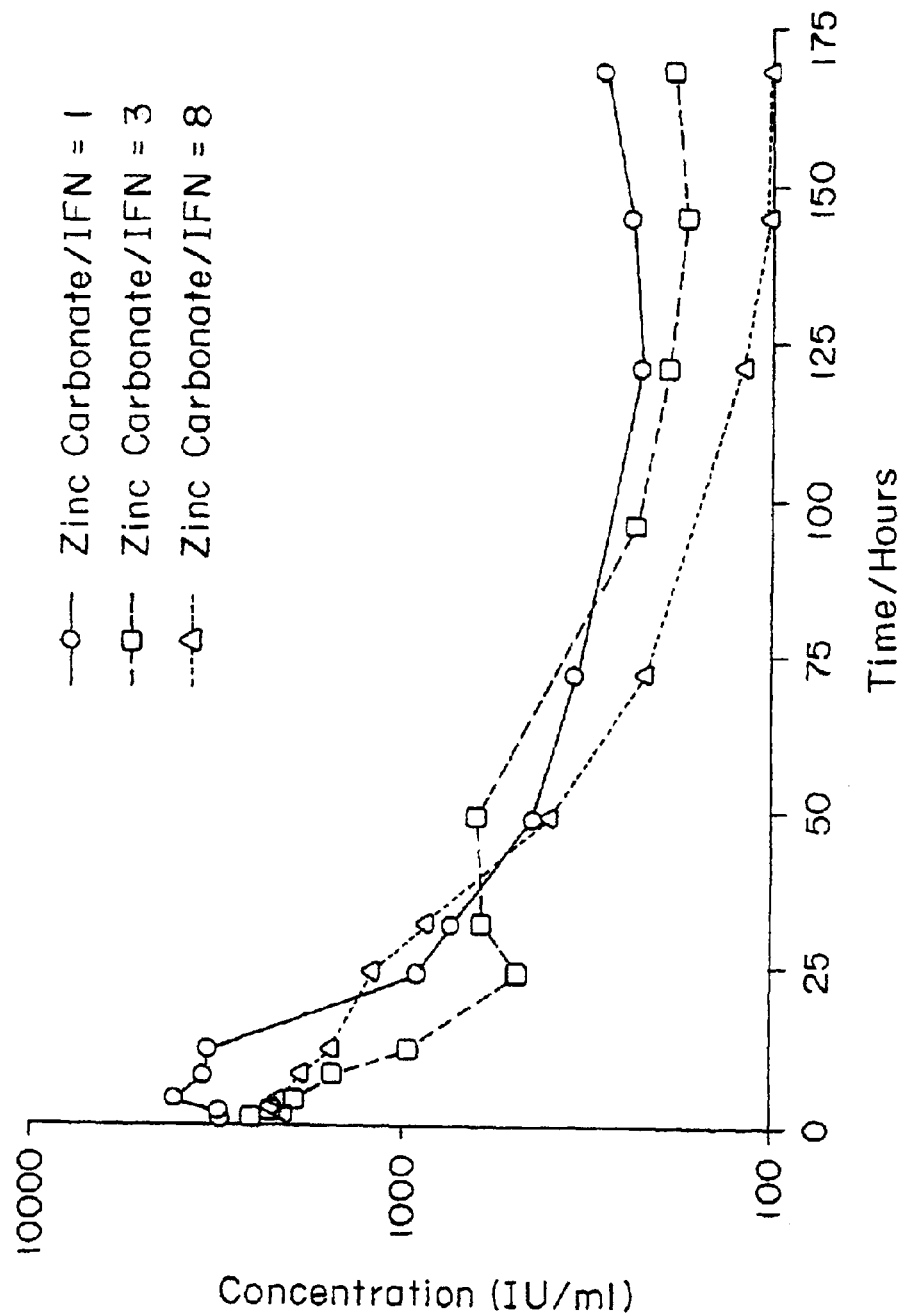
FIG. 8 is a plot of the serum concentration (IU/ml) of IFN-$\alpha$,2b versus time over a 7 day interval in rats which were subcutaneously administered three different IFN-$\alpha$,2b controlled release microspheres of Examples 7 and 8 having zinc carbonate to IFN-$\alpha$,2b ratios of 1:1, 3:1 and 8:1.

For the sustained release test, the weight ratio of zinc carbonate to IFN in microspheres tested were 1:1, 3:1 and 8:1. The sustained release results of this test are presented in FIG. 8. The sustained level observed for the formulation described in Example 8, having a weight ratio of 1:1, was 250±30 IU/ml during days 5–7. The level observed for the formulation, having a weight ratio of 3:1 was 180±10 IU/ml during days 5–7, whereas that for a formulation having a weight ratio of 8:1 was 110±10 IU/ml.

EXAMPLE 12

Effect of Co-Administered Cyclosporin and Hydrocortisone on Pharmacokinetics of Interferon One group of male Sprague-Dawley rats (N=2) (control group), weighing 400±50 g (S.D.) was injected as described in Example 10 with the preferred microspheres of Example 8. An addition group (N=2) of rats (test group) was also given daily intraperitoneal injection of 10 mg cyclosporin A (Sandimmune® Injection, Sandoz, East Hanover, N.J.) and 5 mg hydrocortisone (Spectrum Co., Gardena, Calif.) in 0.5 ml sterilized saline for injection (USP) for days 0 to 14 and then injections twice a week for days 15 to 28. These injections were to suppress the response of the rats' immune systems to the release of IFN-α,2b released in vivo. No antibody titers were detected in these rats for the duration of treatment.

The control group did not receive injections to suppress their immune response to IFN-α,2b. Antibodies were detected after day 7 in these rats.

Figure 9:
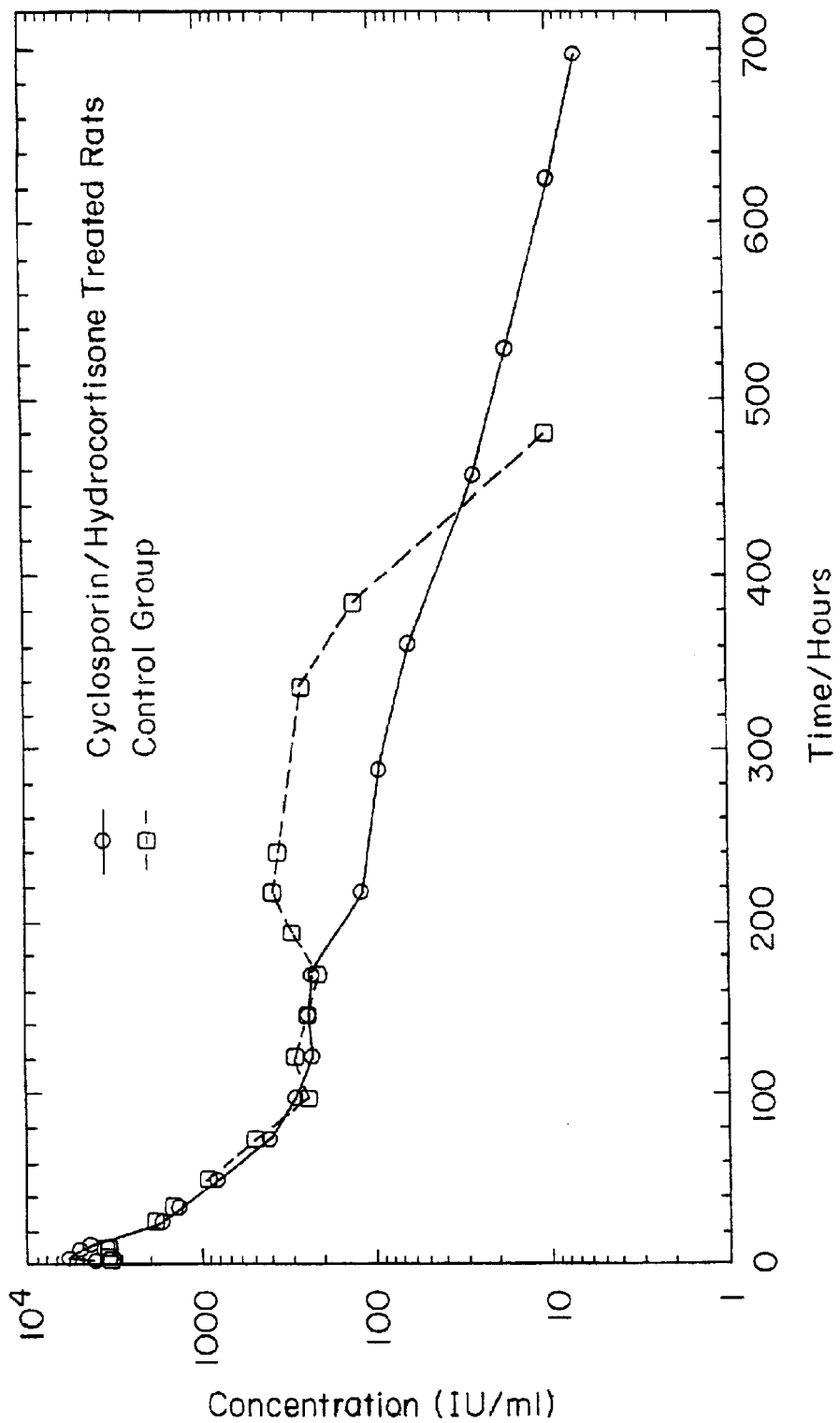
FIG. 9 is a plot of the serum concentration (IU/ml) of IFN-$\alpha$,2b versus time over a 29 day interval in rats which were subcutaneously administered a) IFN-$\alpha$,2b controlled release microspheres of the preferred formulation of Example 8, wherein the rats were immunosuppressed with cyclosporin A and hydrocortisone (two groups) and b) the same formulation of IFN-$\alpha$,2b controlled release microspheres wherein the rats where not immunosuppressed.

The serum levels of IFN-α,2b in the rats of the experimental group and the control group were determined by IRMA through day 29 (696 hours and 480 hours, respectively). These results are provided in FIG. 9. The results for both groups are the same through day 7 suggesting that the cyclosporin A/hydrocortisone treatment does not affect the measured serum concentrations of IFN. The results show that the control group serum levels measured for IFN were artificially high due to their production of antibodies to the IFN-α,2b. The results for the experimental group, in which antibody formation was suppressed, showed sustained release of IFN-α,2b for up to at least 29 days for the preferred microspheres of Example 8.

EXAMPLE 13

In vivo Release of IFN-α,2b from Polymeric Microsphere in Monkeys

Microspheres prepared as in Example 8 (preferred formulation) were tested in a test group of four male cynomolgous monkeys (Charles River Primates) for release of IFN-α,2b. The animals were fed with a standard diet and allowed free access to water. Each monkey was injected subcutaneously with a dose of about 0.12 mg IFN/kg monkey on day zero.

Concurrently, each monkey in a control group of four monkeys, with the same diet and water access as the test group, were subcutaneously injected with an aqueous saline solution containing about 0.12 mg IFN/kg monkey.

Blood samples were taken from the femoral vein at 0, 1, 3, 6, 12, 24, 48, 96, 120, 144, 168, 240, and 336 hours after injection. The IFN-α,2b concentration in the monkey serum samples was determined using both a cytopathic effect assay (CPE; *Pharmacopeial Previews, United States Convention, Inc.*, November–December 1990, page 1241) and IRMA. The CPE results for both groups are provided in FIG. 10.

For the test group, the IRMA and CPE results were similar and showed sustained release of IFN-α,2b from the microspheres.

The CPE and IRMA results for the control group, which received the aqueous IFN-α,2b injection, showed that the IFN-α,2b concentration fell below detectable limits before the second day of testing.

Figure 10:
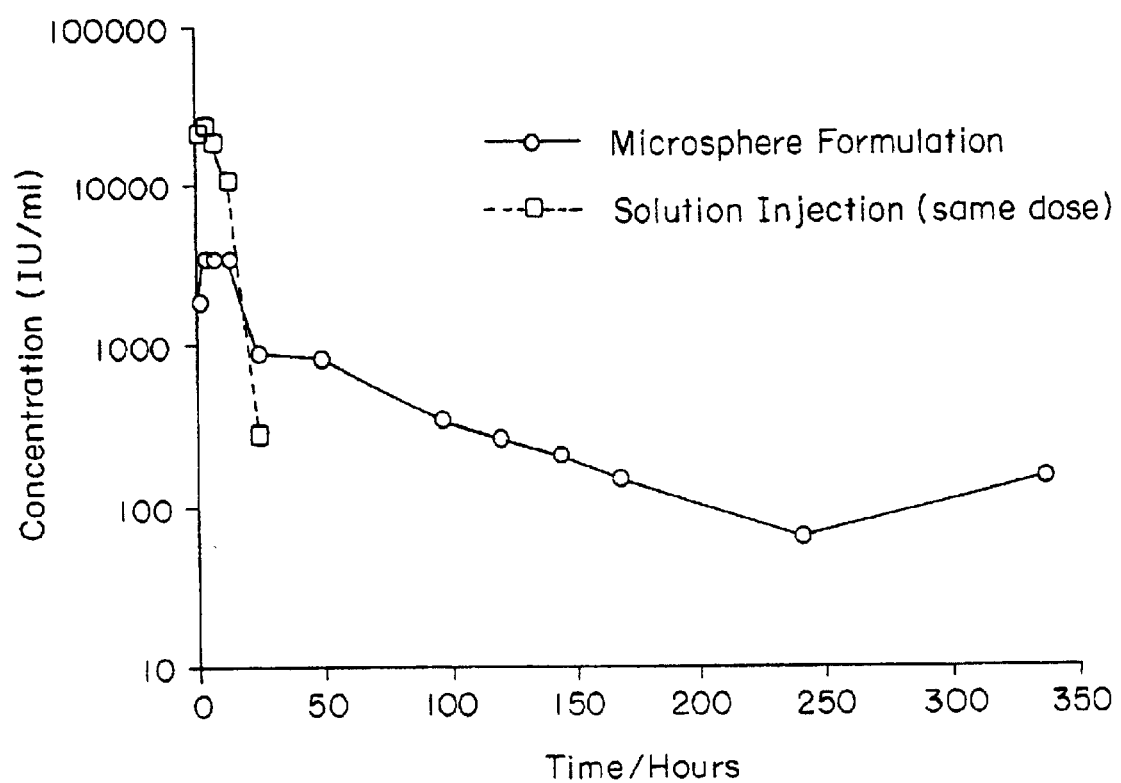
FIG. 10 is a plot of the serum concentrations (IU/ml) of IFN-$\alpha$,2b versus time over a 14 day interval in monkeys which were subcutaneously administered a) IFN-$\alpha$,2b controlled release microspheres of Example 8 having a 5:4 zinc carbonate to IFN-$\alpha$,2b ratio and b) and equal dose of IFN-$\alpha$,2b in 0.9% saline solution.
Figure 11:
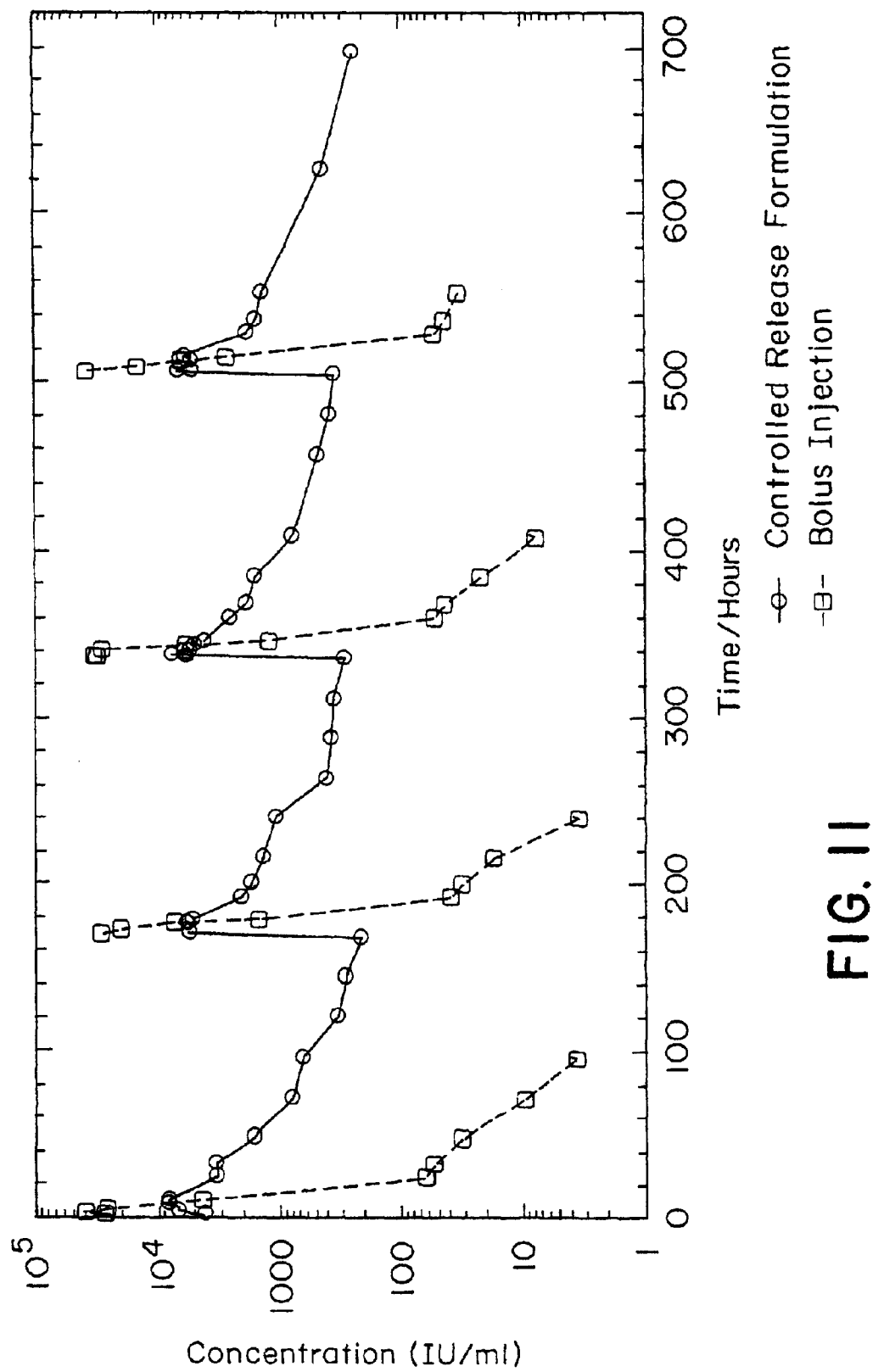
FIG. 11 is a plot of the serum concentrations (IU/ml) of IFN-$\alpha$,2B versus time over a 700-hour interval in rats which were subcutaneously administered four weekly injections of the same dose of a) the preferred formulation of IFN-$\alpha$, 26 controlled release microspheres and b) four weekly bolus injections of IFN-$\alpha$,2b in a 0.9% saline solution.

FIG. 10 shows that the preferred injectable microsphere formulation of Example 8 provided sustained release of biologically active IFN-α.

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition for the controlled release of interferon from a polymeric matrix, comprising:
    a) a biodegradable polymer selected from the group consisting of poly(lactides), poly(glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetals, polycyanoacrylates, polyetheresters, poly (dioxanone)s, poly(alkylene alkylate)s, copolymers of polyethylene glycol and polyorthoester, biodegradable polyurethanes, blends thereof and copolymers thereof; and b) particles of metal cation-complexed interferon, wherein said particles are dispersed within the biodegradable polymer and the interferon is present from about 0.1% (w/w) to about 50% (w/w) of the dry weight of the composition.

2. The composition of claim 1 wherein the interferon is present from about 0.1 (w/w) to about 30% (w/w) of the dry weight of the composition.

3. The controlled release composition of claim 1 wherein the metal cation-to-interferon molar ratio is from about 1:1 and 10:1.

4. The controlled release composition of claim 3 wherein the metal cation to interferon molar ratio is about 2:1.

5. The controlled release composition of claim 1 wherein the metal cation of said metal cation-complexed interferon contains at least one type of biocompatible multivalent cation, wherein said cation is not significantly oxidizing to interferon.

6. The controlled release composition of claim 5 wherein said multivalent cation is selected from the group consisting of $Zn^{+2}$, $Ca^{+2}$, $Cu^{+2}$, $Mg^{+2}$ and combinations thereof.

7. The controlled release composition of claim 1 wherein the interferon is interferon-α.

8. A controlled release composition of claim 1 wherein the biodegradable polymer is a poly(lactide-co-glycolide).

9. A controlled release composition of claim 1 further comprising a second metal cation component, wherein the second metal cation component is not contained in said interferon particles, and wherein the second metal cation component is dispersed within the biocompatible polymer to modulate the release of interferon from the polymeric matrix.

10. A controlled release composition of claim 9 wherein the second metal cation component is selected from the group consisting of magnesium hydroxide, magnesium carbonate, calcium carbonate, zinc carbonate, magnesium acetate, zinc acetate, magnesium sulfate, zinc sulfate, magnesium chloride, zinc chloride, zinc citrate, magnesium citrate and a combination thereof.

* * * * *